United States Patent
Ahn et al.

(10) Patent No.: US 8,500,281 B2
(45) Date of Patent: Aug. 6, 2013

(54) APPARATUS FOR IRRADIATING BEAM AT USER'S EYE GAZE POINT AND OPERATION METHOD THEREOF

(75) Inventors: Chang Geun Ahn, Daejeon (KR); Rae Man Park, Daejeon (KR); Gun Yong Sung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 409 days.

(21) Appl. No.: 12/762,484

(22) Filed: Apr. 19, 2010

(65) Prior Publication Data
US 2011/0043758 A1  Feb. 24, 2011

(30) Foreign Application Priority Data

Aug. 19, 2009 (KR) .................. 10-2009-0076935
Feb. 24, 2010 (KR) .................. 10-2010-0016735

(51) Int. Cl.
*A61B 3/14* (2006.01)
*A61B 3/10* (2006.01)

(52) U.S. Cl.
USPC ............................ 351/209; 351/210; 351/221

(58) Field of Classification Search
USPC ........................................ 351/209, 210, 221
See application file for complete search history.

(56) References Cited

U.S. PATENT DOCUMENTS 5,668,622 A * 9/1997 Charbonnier et al. ........ 351/209
2009/0040460 A1* 2/2009 Bonnin et al. ................ 351/209

FOREIGN PATENT DOCUMENTS

| JP | 2009-157634 A | 7/2009 |
| KR | 10-0520050 B1 | 9/2005 |
| KR | 10-2007-0122337 A | 12/2007 |

* cited by examiner

*Primary Examiner* — Mahidere Sahle

(57) ABSTRACT

There is provided an apparatus for irradiating a beam at a user's eye gaze point and an operation method thereof. The apparatus includes an eye gaze point detecting part analyzing a movement of a user's pupils and detecting the user's eye gaze point, and a beam irradiation part irradiating a beam at the user's eye gaze point detected by the eye gaze point detecting part. The apparatus detects the user's current eye gaze point and irradiates the beam at the user's detected eye gaze point, thereby allowing for the performance of desired control with greater accuracy.

17 Claims, 5 Drawing Sheets

APPARATUS FOR IRRADIATING BEAM AT USER'S EYE GAZE POINT AND OPERATION METHOD THEREOF

CROSS-REFERENCE TO RELATED APPLICATIONS

This application claims the priorities of Korean Patent Application Nos. 10-2009-0076935 filed on Aug. 19, 2009 and 10-2010-0016735 filed on Feb. 24, 2010, in the Korean Intellectual Property Office, the disclosure of which is incorporated herein by reference.

BACKGROUND OF THE INVENTION

1. Field of the Invention

The present invention relates to an apparatus for irradiating a beam at a user's eye gaze point, and more particularly, to an apparatus for irradiating a beam at a user's eye gaze point in order to perform a controlling operation with greater accuracy.

2. Description of the Related Art

Technologies for controlling the operation of electronic devices by tracking a user's eyes or eye gaze point have been continuously developed and proposed.

A conventional system for tracking eye gaze point basically senses only the movement of a user's pupils and detects the user's eye gaze point upon which the user is focusing.

However, the conventional method lacks accuracy in controlling operations using the user's eyes or eye gaze point, because the conventional method has difficult in detecting accurate a movement of a user's pupils and a movement of the user's head at the same time.

Also, in order to perform the controlling operation of a device through the detection of the user's eye gaze point, information related to the user's eye gaze point must be obtained and the information obtained must then be transferred to the device. For this reason, interfacing with the device must be required.

SUMMARY OF THE INVENTION

An aspect of the present invention provides an apparatus for detecting an eye gaze point upon which the user is focusing by analyzing a movement of a user's pupils and irradiating a beam at the user's detected eye gaze point and an operation method thereof.

An aspect of the present invention also provides an apparatus for irradiating a beam at the user's detected eye gaze point and allowing such a beam irradiation to be utilized as an input signal of a control target device, and an operation method thereof.

According to an aspect of the present invention, there is provided an apparatus for irradiating a beam at a user's eye gaze point, the apparatus including: an eye gaze point detecting part analyzing a movement of a user's pupils and detecting the user's eye gaze point; and a beam irradiation part irradiating a beam at the user's eye gaze point detected by the eye gaze point detecting part.

The eye gaze point detecting part may include a pupil movement detecting part detecting the movement of the user's pupils; a synchronizing part obtaining synchronizing information allowing the user's eye gaze point to coincide with a beam irradiation location; and an eye gaze point variation calculating part analyzing the movement of the user's pupils according to the synchronizing information and calculating a user's eye gaze point variation.

The synchronizing part may obtain the synchronizing information related to coordinates of the user's pupils measured when the user's eye gaze point coincides with the beam irradiation location.

The eye gaze point detecting part may further include a compensation calculating part obtaining a compensation value in order to remove an error between the calculated eye gaze point variation and an actual eye gaze point variation.

The compensation calculating part may calculate the compensation value on the basis of the calculated eye gaze point variation and the actual eye gaze point variation when the user's eye gaze point moves from a first point to a second point preset with a spaced distance and direction therebetween.

The eye gaze point variation calculating part may compensate for the user's eye gaze point variation on the basis of the compensation value.

The beam irradiation part may include a beam light source irradiating the beam; and a beam irradiation location controlling part controlling the beam irradiation location according to the user's eye gaze point variation and allowing the beam to be irradiated at the user's eye gaze point.

The apparatus may further include a beam reactive part detecting the beam irradiated by the beam irradiation part and generating a signal having information corresponding to a beam irradiation location.

The beam reactive part may include a beam detecting part detecting the beam irradiated by the beam irradiation part and obtaining the beam irradiation location; and an input signal generating part generating the signal having the information corresponding to the beam irradiation location and providing the signal to a control target device.

According to another aspect of the present invention, there is provided a method of operating an apparatus for irradiating a beam at a user's eye gaze point, the method including: synchronizing a user's eye gaze point with a beam irradiation location; identifying the user's current eye gaze point by analyzing a movement of a user's pupils; and irradiating a beam at the user's current eye gaze point.

The synchronizing of the user's eye gaze point with the beam irradiation location may include obtaining synchronizing information related to coordinates of the user's pupils measured when the user's eye gaze point coincides with the beam irradiation location.

The identifying of the user's current eye gaze point may include detecting the movement of the user's pupils; and analyzing the movement of the user's pupils according to the synchronizing information and calculating a user's eye gaze point variation.

The irradiating of the beam may include allowing the beam to be irradiated at the user's eye gaze point by controlling the beam irradiation location according to the user's eye gaze point variation.

The method may further include obtaining a compensation value in order to remove an error between a calculated eye gaze point variation and an actual eye gaze point variation before identifying the user's current eye gaze point.

The identifying of the user's current eye gaze point may include detecting the movement of the user's pupils; analyzing the movement of the user's pupils according to the synchronizing information and calculating the user's eye gaze point variation; and removing the error between the eye gaze point variation calculated according to the compensation value and the actual eye gaze point variation.

The method may further include generating a signal having information corresponding to the beam irradiation location by detecting the beam irradiation location.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
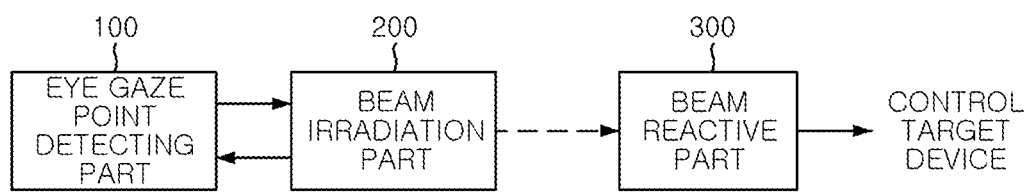
FIG. 1 is a block diagram illustrating an apparatus for irradiating a beam at a user's eye gaze point according to an exemplary embodiment of the present invention.

Exemplary embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In describing the present invention, if a detailed explanation for a related known function or construction is considered to unnecessarily divert the gist of the present invention, such explanation will be omitted but would be understood by those skilled in the art.

In order to clarify the present invention, parts irrelevant to the description of the present invention are omitted, and the same reference numerals will be used throughout to designate the same or like elements.

In addition, unless explicitly described to the contrary, the word "include" and variations such as "includes" or "including," will be understood to imply the inclusion of stated elements but not the exclusion of any other elements.

FIG. 1 is a block diagram illustrating an apparatus for irradiating a beam at a user's eye gaze point according to an exemplary embodiment of the present invention.

Referring to FIG. 1, an apparatus for irradiating a beam at a user's eye gaze point (hereinafter, also referred to as a "beam irradiation apparatus") according to this embodiment includes an eye gaze point detecting part 100 and a beam irradiation part 200 which are configured as a headset device worn on a user's head, and a beam reactive part 300 disposed in the front side of a control target device in order to facilitate the reception of a beam irradiated from the beam irradiation part 200.

The eye gaze point detecting part 100 detects an eye gaze point where the user is looking by sensing the movement of the user's pupils.

The beam irradiation part 200 controls a beam irradiation location (i.e. angle and direction) to thereby irradiate the beam at the user's eye gaze point which is detected by the eye gaze point detecting part 100.

The beam reactive part 300 detects the location of the irradiated beam, generates a signal having information corresponding thereto (i.e. the coordinates of the location of the irradiated beam, ID (identifier) related to an object disposed at the location of the irradiated beam, or the like), and provides the signal to the control target device.

The control target device receives the signal, provided by the beam irradiation apparatus 100, as an input signal and performs the user's desired operation in response to the input signal.

Here, the control target device may be an electronic device such as a TV, a computer and a cellular phone that the user desires to remotely control.

For example, in the case that the control target device is a TV and the user desires to control a TV power switch, the beam reactive part 300 is attached onto the power switch, and the user gazes at the power switch in order to cause a beam to be irradiated onto the power switch. Then, the TV detects whether or not the beam is irradiated onto the power switch through the beam reactive part 300, and controls the power of the TV according to the detection result.

Figure 2:
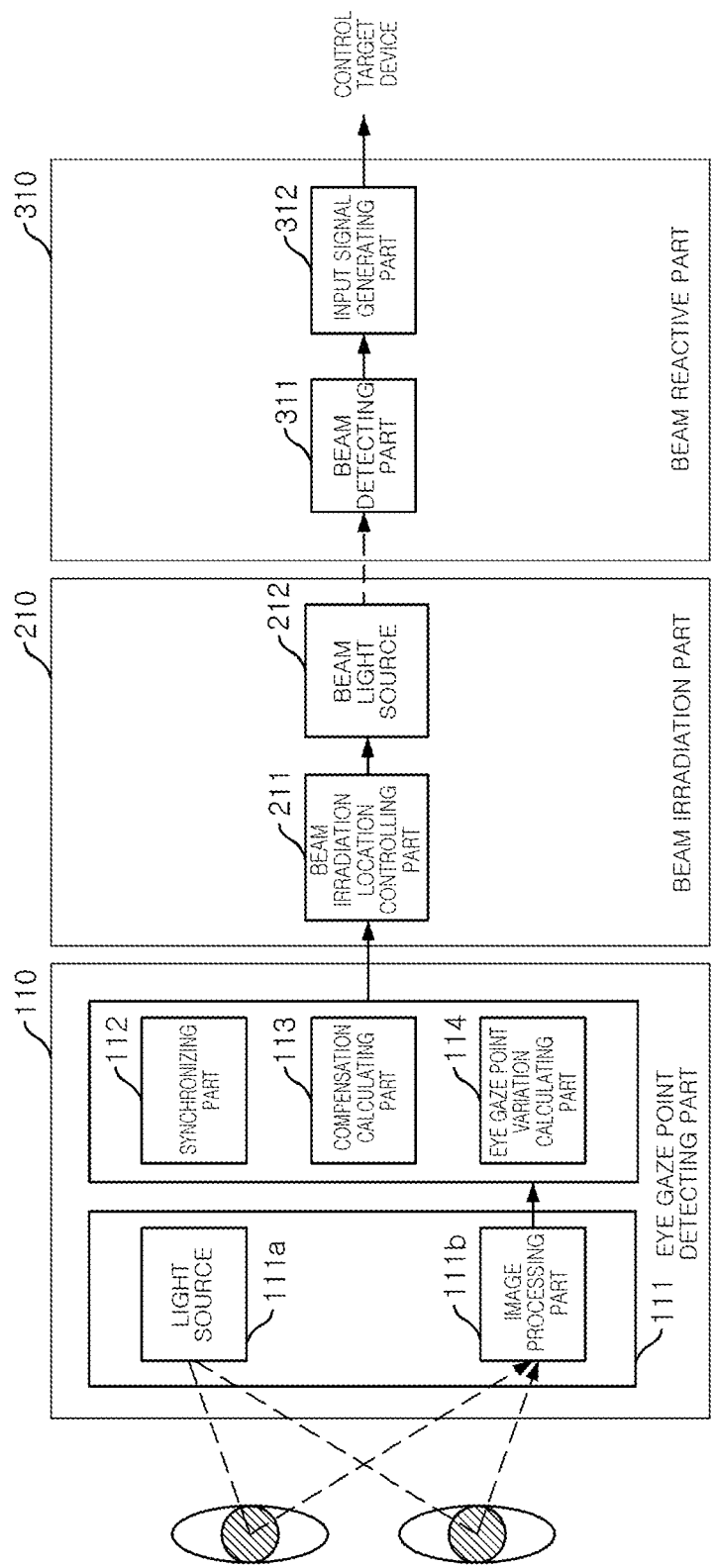
FIG. 2 is a detailed block diagram illustrating an apparatus for irradiating a beam at a user's eye gaze point according to an exemplary embodiment of the present invention.

FIG. 2 is a detailed block diagram illustrating an apparatus for irradiating a beam at a user's eye gaze point according to an exemplary embodiment of the present invention.

Referring to FIG. 2, an eye gaze point detecting part 110 includes a pupil movement detecting part 111, a synchronizing part 112, a compensation calculating part 113, and an eye gaze point variation calculating part 114. A beam irradiation part 210 includes a beam irradiation location controlling part 211 and a beam light source 212. A beam reactive part 310 includes a beam detecting part 311 and an input signal generating part 312.

Hereinafter, functions of each element will be described in detail.

The pupil movement detecting part 111 includes light sources 111a disposed adjacent to the user's pupils or in contact with the user's pupils, and an image processing part 111b. The light sources 111a are used to irradiate light onto the user's pupils, respectively. The image processing part 111b detects the movement of the user's pupils by obtaining and processing an image of the user's pupils.

Here, the image processing part 111b detects the movement of the user's pupils by using existing methods such as a method of detecting the location of light reflected from the pupils, a method of detecting an amount of light reflected from the pupils, or a method of interpreting an image signal using an image sensor. A detailed description thereof is therefore omitted.

In order to allow the beam irradiation location to be synchronized with the user's eye gaze point, the synchronizing part 112 allows the beam irradiation location to coincide with the user's eye gaze point, and then obtains synchronizing information related to the coordinates of the pupils at this time.

Prior to synchronization, the beam is basically fixed toward the user's face without indicating the user's eye gaze point. Therefore, the user gazes at the beam irradiation location and requests the synchronizing part 112 to obtain synchronizing information. In response to that request, the synchronizing part 112 obtains the synchronizing information related to the coordinates of the pupils measured when the user's eye gaze point coincides with the beam irradiation location, and allows the beam irradiation location to follow the user's eye gaze point on the basis of the synchronizing information.

Figure 3A:
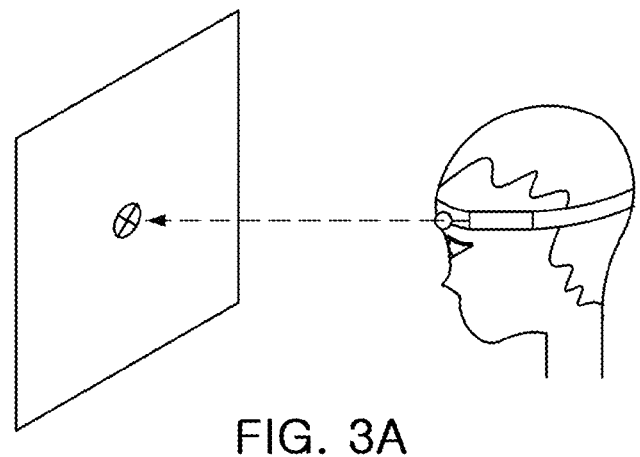
FIGS. 3A and 3B illustrate processes of obtaining synchronizing information allowing a user's eye gaze point to coincide with a beam irradiation location according to an exemplary embodiment of the present invention.
Figure 3B:
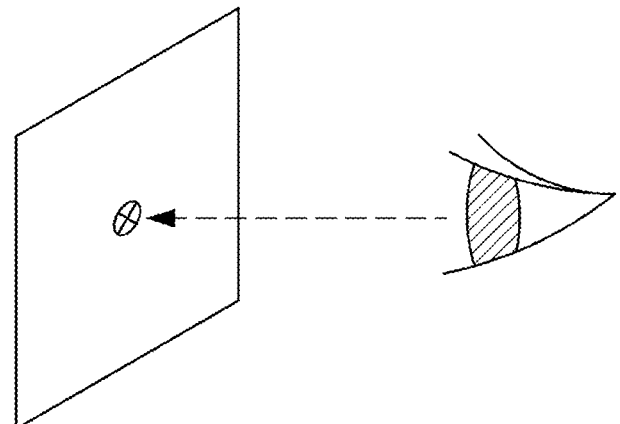

For example, after the user moves his or her head to cause the beam to be irradiated at a predetermined point as shown in FIG. 3a, the user gazes at the corresponding point as shown in FIG. 3b, and the synchronizing part 112 then obtains the coordinates of the pupils at this time as the synchronizing information. In another method, after the beam is irradiated at any point, the coordinates of the pupils measured when the user gazes at the corresponding point may be obtained as the synchronizing information.

The compensation calculating part 113 obtains a compensation value in order to allow the eye gaze point variation, calculated by the eye gaze point variation calculating part 114, to coincide with an actual eye gaze point variation.

Figure 3C:
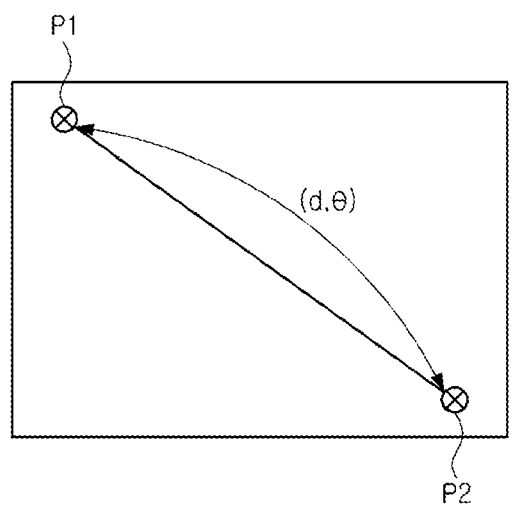
FIG. 3C illustrates processes of obtaining a compensation value allowing a user's eye gaze point variation to coincide with a beam movement distance according to an exemplary embodiment of the present invention.

There may be an error between the eye gaze point variation, calculated when the beam is moved according to the user's eye gaze point, and the actual eye gaze point variation. Accordingly, while allowing the user's eye gaze point to move from a first point P1 to a second point P2 where the spaced distance and direction d and θ therebetween are preset as shown in FIG. 3c, the compensation calculating part 113 obtains the relationship between the eye gaze point variation, calculated by the eye gaze point variation calculating part 114, and the spaced distance and direction d and θ of the first and second points P1 and P2 (i.e. actual eye gaze point variation). On the basis of the obtained relationship, the compensation calculating part 113 calculates the compensation value which allows the eye gaze point variation, calculated by the eye gaze point variation calculating part 114, to coincide with the actual eye gaze point variation.

The eye gaze point variation calculating part 114 obtains the coordinates of the pupils corresponding to the movement of the pupils according to sampling period, compares the obtained coordinates with the coordinates of the pupils obtained as the synchronizing information, and calculates the variation in the movement of the pupils. Then, the eye gaze point variation calculating part 114 calculates the eye gaze point variation on the basis of the variation in the movement of the pupils, additionally removes an error between the eye gaze point variation calculated using the compensation value and the actual eye gaze point variation, and provides the result to the beam irradiation part 210.

The beam irradiation location controlling part 211 controls the location which the beam light source 212 irradiates (i.e. beam irradiation angle and direction), up/down and left/right, according to the user's eye gaze point variation provided by the eye gaze point variation calculating part 114, to thereby allow the beam to be irradiated at the user's eye gaze point.

The beam light source 212 is realized as a laser beam, and irradiate's the beam at the user's eye gaze point under the control of the beam irradiation location controlling part 211. Here, a type of beam may be variable according to the usage of the beam irradiation apparatus. Generally, considering the straightness and direction of the beam, a laser beam is appropriate. In addition, the laser beam may be invisible to the naked eye due to being irradiated in rapid pulses for a very short time or utilizing light in the deep infrared wavelength or the like.

The beam detecting part 311 detects and reports the location where the beam is irradiated by including at least one or more light-receiving sensors (e.g. photo-sensor or photo-detector) disposed in the front side of the control target device and capable of detecting a beam of specific wavelength that is irradiated through the beam light source 212.

The input signal generating part 312 generates an input signal having information (i.e. the coordinates of the location of the irradiated beam, ID related to an object disposed at the location of the irradiated beam, or the like) corresponding to the location of the irradiated beam detected by the beam detecting part 311 and provides the input signal to the control target device.

In this embodiment, a single beam irradiation part is included. If desired, two beam irradiation parts may be realized as shown in FIG. 4.

Figure 4:
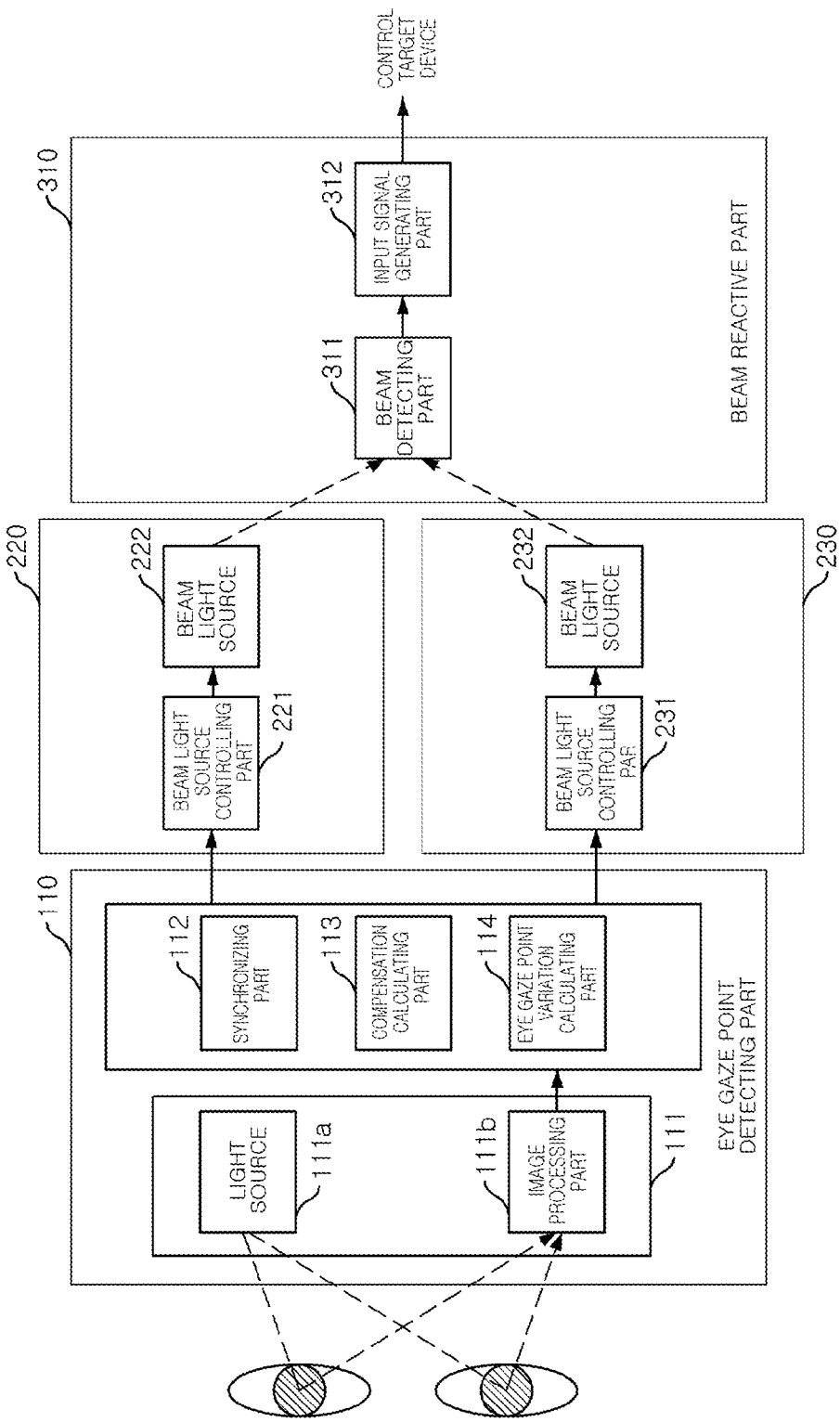
FIG. 4 is a detailed block diagram illustrating an apparatus for irradiating a beam at a user's eye gaze point according to another exemplary embodiment of the present invention.

FIG. 4 is a detailed block diagram illustrating an apparatus for irradiating a beam at a user's eye gaze point according to another exemplary embodiment of the present invention.

Referring to FIG. 4, the eye gaze point detecting part 110 and the beam reactive part 130 are configured to be identical to those in FIG. 3. However, two beam irradiation parts 220 and 230 are installed to correspond to the respective eyes.

Here, first and second beam irradiation parts 220 and 230 receive information related to the eye gaze point of the respective eyes from the eye gaze point detecting part 120, and irradiate beams at the eye gaze point of the respective eyes.

In the case of the realization of two beam irradiation parts, through the calculation of variations in beam irradiation location, the distance between the user (especially, the user's head) and the eye gaze point may be calculated using simple trigonometry.

When the distance between the synchronized eye gaze point and the user changes, the coordinates of the user's pupils do not move in the same direction, but have bilateral symmetry and move in a direction based on the center point of the user's eyes. That is, when the user is closer to the eye gaze point, the coordinates of the user's pupils move toward the center point of the user's eyes. When the user is farther away from the eye gaze point, the coordinates of the user's pupils move in a direction opposed thereto. In the case of using these features, through the calculation of variations in beam irradiation location, the distance between the user and the eye gaze point can be calculated using simple trigonometry.

If the distance between the user and the eye gaze point can be calculated, an actual distance between two eye gaze points where the user gazes is also calculated. That is, in the case that the user moves his or her eye gaze point and gazes at a new point, since the distance between the new point and the user is calculated in the same manner as described above and the variation in beam irradiation location is also calculated, the actual distance between the two eye gaze points where the user gazes can be easily calculated.

Figure 5:
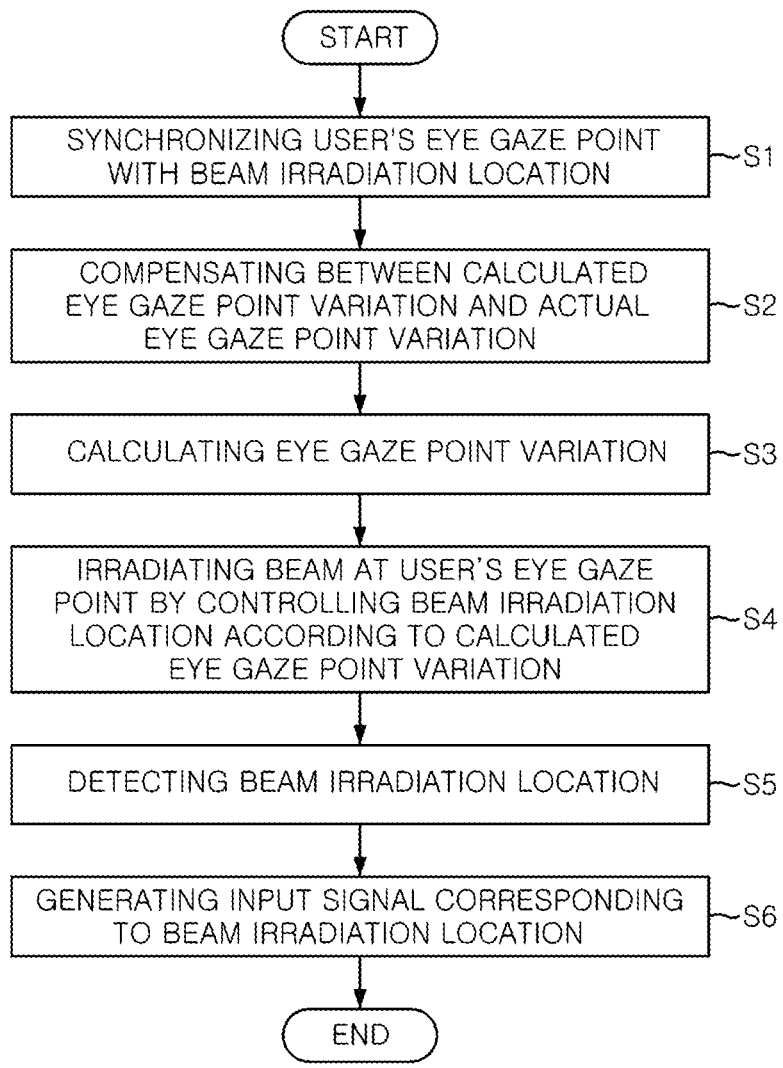
FIG. 5 is a flowchart illustrating a method of operating an apparatus for irradiating a beam at a user's eye gaze point according to an exemplary embodiment of the present invention.

FIG. 5 illustrates a method of operating an apparatus for irradiating a beam at a user's eye gaze point according to an exemplary embodiment of the present invention.

First of all, a beam irradiation location in an initial state is unconditionally set toward a user's face irrespective of the user's eye gaze point, so an eye gaze point detecting part is required to synchronize the user's eye gaze point with the beam irradiation location in order to allow a beam to be irradiated at the user's eye gaze point. Accordingly, the eye gaze point detecting part obtains synchronizing information related to the coordinates of the user's pupils measured when the user's eye gaze point coincides with the beam irradiation location in operation S1.

Also, in order to perform more accurate beam control, the eye gaze point detecting part additionally obtains a compensation value which allows a calculated eye gaze point variation to coincide with an actual eye gaze point variation in operation S2.

After completing the synchronization and the obtainment of the compensation value in operations S1 and S2, the beam is ready to be irradiated at the user's eye gaze point.

At this time, the eye gaze point detecting part analyzes the movement of the user's pupils according to the synchronizing information and calculates the user's eye gaze point variation, and then removes an error between the eye gaze point variation calculated according to the compensation value and the actual eye gaze point variation in operation S3.

After that, a beam irradiation part changes the beam irradiation location according to the user's eye gaze point variation calculated in operation S3, and irradiates the beam at the user's current eye gaze point in operation S4.

When the beam is irradiated at the user's current eye gaze point (e.g. a specific location on a monitor of a control target device), a beam reactive part disposed in the front side of the control target device detects the location of the irradiated beam in operation S5. Then, the beam reactive part generates an input signal in order to report an object (e.g. a menu bar, an icon, or a button) disposed at the corresponding location and provides the input signal to the control target device in operation S6.

As described above, according to exemplary embodiments of the invention, the user's current eye gaze point is visually and clearly recognized by irradiating the beam at the user's eye gaze point rather than merely estimating the user's eye gaze point.

Accordingly, when the control target device receives the input signal from the beam irradiation apparatus according to exemplary embodiments of the invention, it is allowed to identify and perform the user's desired operation and service with greater accuracy.

For example, in the case that a computer (control target device) has a beam reactive part disposed on the front side of a computer monitor and A to N program icons are displayed on the computer monitor, when a user gazes at the A program icon, a beam irradiation part irradiates a beam at the A program icon. Then, the beam reactive part generates a signal for selecting the A program icon, and thus the computer performs the operation of the A program in response to the signal.

As set forth above, according to an apparatus for irradiating a beam at a user's eye gaze point and an operation method thereof, a beam is irradiated at an user's current eye gaze point through the apparatus for irradiating a beam at a user's eye gaze point having spatial coordinates identical to those of the user's head. Therefore, the user's current eye gaze point is detected more clearly and the accuracy of control is improved.

Also, allowing the beam irradiated at the user's eye gaze point to be used as an input signal and allowing various devices within the user's field of vision to be controlled leads to a great expansion of the applications of the apparatus for irradiating the beam at the user's eye gaze point.

While the present invention has been shown and described in connection with the exemplary embodiments, it will be apparent to those skilled in the art that modifications and variations can be made without departing from the spirit and scope of the invention as defined by the appended claims.

What is claimed is:

1. An apparatus for radiating a beam to an eye gaze point, the apparatus comprising:
    an eye gaze point detecting part configured to analyze a movement of a user's pupils, and detect the eye gaze point based on the movement of the user's pupils; and
    a beam radiation part configured to radiate the beam to the eye gaze point detected by the eye gaze point detecting part,
    wherein the beam radiation part comprises:
    a beam light source configured to radiate the beam; and
    a beam radiation location controlling part configured to control a beam radiation location according to an eye gaze point variation provided by an eye gaze point variation calculating part, so that the beam is radiated to the eye gaze point.

2. The apparatus of claim 1, wherein the eye gaze point detecting part comprises:
    a pupil movement detecting part configured to detect the movement of the user's pupils;
    a synchronizing part configured to obtain synchronizing information measured when the eye gaze point coincides with a predetermined beam radiation location; and
    the eye gaze point variation calculating part configured to analyze the movement of the user's pupils using the synchronizing information, and to calculate the eye gaze point variation.

3. The apparatus of claim 2, wherein the synchronizing part is configured to obtain the synchronizing information, including coordinates of the user's pupils measured when the eye gaze point coincides with the predetermined beam radiation location.

4. The apparatus of claim 2, wherein the eye gaze point detecting part further comprises a compensation calculating part configured to obtain a compensation value to remove an error between the calculated eye gaze point variation and an actual eye gaze point variation.

5. The apparatus of claim 4, wherein the compensation calculating part is configured to calculate the compensation value using the calculated eye gaze point variation and the actual eye gaze point variation when the eye gaze point moves from a first predetermined point to a second predetermined point.

6. The apparatus of claim 5, wherein the eye gaze point variation calculating part is configured to calculate the eye gaze point variation further using the compensation value.

7. The apparatus of claim 1, further comprising a beam reactive part configured to detect the beam radiated by the beam radiation part, and to generate a signal including information corresponding to a beam radiation location.

8. The apparatus of claim 7, wherein the beam reactive part comprises:
    a beam detecting part configured to detect the beam radiated by the beam radiation part and to obtain the beam radiation location; and
    an input signal generating part configured to generate the signal including the information corresponding to the beam radiation location and to provide the signal to a control target device.

9. A method of operating an apparatus for radiating a beam to an eye gaze point, the method comprising:
    synchronizing the eye gaze point with a predetermined beam radiation location;
    identifying a current eye gaze point by analyzing a movement of a user's pupils; and
    radiating a beam to the current eye gaze point,
    wherein the radiating of the beam comprises controlling a beam radiation location based on eye gaze point variation so that the beam is radiated to the eye gaze point.

10. The method of claim 9, wherein the synchronizing of the eye gaze point with the predetermined beam radiation location comprises obtaining synchronizing information, the synchronizing information including coordinates of the user's pupils measured when the eye gaze point coincides with the predetermined beam radiation location.

11. The method of claim 10, wherein the identifying of the current eye gaze point comprises:
    detecting the movement of the user's pupils;

analyzing the movement of the user's pupils using the synchronizing information; and calculating an eye gaze point variation.

12. The method of claim 10, further comprising obtaining a compensation value in order to remove an error between a calculated eye gaze point variation and an actual eye gaze point variation.

13. The method of claim 12, wherein the identifying of the current eye gaze point comprises:

detecting the movement of the user's pupils;

analyzing the movement of the user's pupils using the synchronizing information;

calculating the eye gaze point variation; and removing the error between the calculated eye gaze point variation and the actual eye gaze point variation using the compensation value.

14. The method of claim 9, further comprising:

detecting a beam radiation location; and generating a signal including information corresponding to the beam radiation location.

15. The apparatus of claim 1, wherein the eye gaze point detecting part and the beam radiation part are included on a headset device.

16. An apparatus for radiating a beam to an eye gaze point, the apparatus comprising:

an eye gaze point detecting part configured to analyze a movement of a user's pupils, and detect the eye gaze point based on the movement of the user's pupils, the eye gaze point detecting part including a compensation calculating part configured to obtain a compensation value to remove an error between a calculated eye gaze point variation and an actual eye gaze point variation; and a beam radiation part configured to radiate the beam to the eye gaze point detected by the eye gaze point detecting part.

17. The apparatus of claim 1, wherein the eye gaze point detecting part and the beam radiation part are partially included in a headset device.

* * * * *